(12) United States Patent
Waechter-Stehle et al.

(10) Patent No.: US 9,098,899 B2
(45) Date of Patent: Aug. 4, 2015

(54) DETERMINING THE SPECIFIC ORIENTATION OF AN OBJECT

(75) Inventors: Irina Waechter-Stehle, Hamburg (DE); Reinhard Kneser, Aachen (DE); Helko Lehmann, Aachen (DE); Jurgen Weese, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 261 days.

(21) Appl. No.: 13/699,351

(22) PCT Filed: May 18, 2011

(86) PCT No.: PCT/IB2011/052178
§ 371 (c)(1),
(2), (4) Date: Nov. 21, 2012

(87) PCT Pub. No.: WO2011/148299
PCT Pub. Date: Dec. 1, 2011

(65) Prior Publication Data
US 2013/0071001 A1 Mar. 21, 2013

(30) Foreign Application Priority Data
May 27, 2010 (EP) ..................................... 10164181

(51) Int. Cl.
*G06K 9/00* (2006.01)
*G06T 7/00* (2006.01)
(Continued)

(52) U.S. Cl.
CPC .................. *G06T 7/0012* (2013.01); *A61B 6/12* (2013.01); *A61B 6/5247* (2013.01); *A61B 8/0841* (2013.01); *A61B 8/4416* (2013.01); *A61B 19/54* (2013.01); *G06T 7/0042* (2013.01); *A61B 8/0833* (2013.01); *A61B 19/5225* (2013.01); *A61B 2019/524* (2013.01); *A61B 2019/5242* (2013.01); *A61B 2019/5425* (2013.01); *A61B 2019/5454* (2013.01); *A61B 2019/5466* (2013.01); *A61B 2019/5495* (2013.01); *A61F 2/2418* (2013.01);
(Continued)

(58) Field of Classification Search
None
See application file for complete search history.

(56) References Cited

U.S. PATENT DOCUMENTS 5,951,475 A * 9/1999 Gueziec et al. ............... 600/425
6,493,575 B1 12/2002 Kesten et al.
(Continued)

FOREIGN PATENT DOCUMENTS

WO WO0130254 5/2001
WO WO2006114721 11/2006

OTHER PUBLICATIONS

G. Tripathi, "Optimal Stent Placement with Reduced X-Ray Exposure", Siemens AG 2009.
"Visualization Markers for Implantable Medical Devices and/or Tools".

*Primary Examiner* — Shervin Nakhjavan (57) ABSTRACT

The present invention relates to the determination of the specific orientation of an object. In order to provide enhanced positioning information of an object to a user, a medical imaging system and a method for operating of a medical imaging system are proposed wherein 2D image data (14) of an object is acquired (12) with an imaging system, wherein the object is provided with at least three markers visible in the 2D image; and wherein (16) the markers are detected in the 2D image; and wherein the spatial positioning and rotation angle (20) of the object in relation to the system geometry is identified (18) on behalf of the markers; and wherein an object-indicator (24) is displayed (22) indicating the spatial positioning and rotation angle of the object.

23 Claims, 11 Drawing Sheets

(51) Int. Cl.
  _A61B 6/12_   (2006.01)
  _A61B 6/00_   (2006.01)
  _A61B 8/00_   (2006.01)
  _A61B 8/08_   (2006.01)
  _A61B 19/00_   (2006.01)
  _A61F 2/24_   (2006.01)
  _A61F 2/82_   (2013.01)
(52) U.S. Cl.
  CPC ........... _A61F 2/82_ (2013.01); _A61F 2250/0098_ (2013.01); _G06T 2207/10088_ (2013.01); _G06T 2207/10116_ (2013.01); _G06T 2207/10132_ (2013.01); _G06T 2207/30052_ (2013.01); _G06T 2207/30101_ (2013.01); _G06T 2207/30204_ (2013.01)

(56) References Cited

U.S. PATENT DOCUMENTS

| | | | |
|---|---|---|---|
| 8,437,449 B2* | 5/2013 | Riley et al. | 378/65 |
| 2001/0034480 A1* | 10/2001 | Rasche et al. | 600/407 |
| 2004/0002642 A1* | 1/2004 | Dekel et al. | 600/407 |
| 2004/0054403 A1 | 3/2004 | Israel | |
| 2004/0122311 A1* | 6/2004 | Cosman | 600/427 |
| 2005/0107808 A1* | 5/2005 | Evans et al. | 606/139 |
| 2006/0058647 A1 | 3/2006 | Strommer | |
| 2008/0147174 A1* | 6/2008 | Konstantino et al. | 623/1.35 |
| 2009/0198126 A1* | 8/2009 | Klingenbeck-Regn | 600/426 |
| 2009/0310832 A1* | 12/2009 | Kim | 382/128 |
| 2010/0094124 A1 | 4/2010 | Schoonenberg et al. | |

\* cited by examiner

DETERMINING THE SPECIFIC ORIENTATION OF AN OBJECT

FIELD OF THE INVENTION

The present invention relates to the determination of the specific orientation of an object. In particular, the present invention relates to a medical imaging system and a method for operating of a medical imaging system as well as computer program element for controlling a medical imaging system and to computer readable medium having stored such a computer program element.

BACKGROUND OF THE INVENTION

For determining the position of an object located in a region of interest, medical imaging systems provide two-dimensional image data to a user. From WO 2006/114721 A2, a method is known wherein a tool is provided with markers which are visible in the images acquired by an imaging system. From the marker location information in the images, the tool location information can be derived. But two markers do not provide any rotational information.

SUMMARY OF THE INVENTION

As a further disadvantage, the markers do not necessarily give straight forward information about the actual positioning of the object to the user. In particular with respect to asymmetric objects, there is thus a need to provide information about the proper actual rotation to the user.

It is an object of the present invention to provide enhanced positioning information of an object to a user.

The object of the present invention is solved by the subject-matter of the independent claims, wherein further embodiments are incorporated in the dependent claims.

It should be noted that the following described aspects of the invention apply also for the medical imaging system, the method, the program element, and the computer readable medium.

According to an aspect of the invention, a medical imaging system comprises image acquisition means, a data processing unit, and a display. The acquisition means are adapted to acquire 2D image data of an object, wherein the object is provided with at least three markers visible in the 2D image. The data processing unit is adapted to detect the markers in the 2D image and to identify the spatial positioning and rotation angle of the object in relation to the system geometry on behalf of the markers. The display is adapted to display an object indicator indicating the spatial positioning and rotation angle of the object.

According to another aspect of the invention, a method for operating a medical imaging system is provided, comprising the following steps: a) acquiring 2D image data of an object with an imaging system, wherein the object is provided with at least three markers visible in the 2D image; b) detecting the markers in the 2D image; c) identifying the spatial positioning and rotation angle of the object in relation to the system geometry on behalf of the markers; and d) displaying an object indicator indicating the spatial positioning and rotation angle of the object.

Within the context of the present invention, the term "rotation" relates to the rotation around the axis of an object. The term "positioning" or position relates to the location in space, i.e. the three-dimensional location or position.

The object indicator provides straight forward information, i.e. information that does not need any decoding or spatial imagination steps by the user such that the user is provided with direct information and is only distracted from other procedural steps in a minimized way. Thus, the concentration of the user is not further absorbed so that the user can focus on his actual tasks, which, for example, concerning surgeons in a hospital can be advantageous.

According to another aspect of the invention, a 3D image is registered with the 2D image data, and the object indicator is displayed together with the image data of the registered 3D and 2D images.

This provides the advantage that the user is provided with spatial positioning information of the object in relation to a volume or region of interest surrounding the object. In other words, the spatial information comprising both positioning and rotation information of the object is provided in an enhanced spatial context by the 3D image information.

According to another aspect of the invention, before step a), a desired spatial positioning and rotation angle of the object is predetermined and a configuration of the markers for the desired position is computed. Further, a projection of the computed marker configuration is generated according to the system geometry during the acquisition of a 2D image in step a). Furthermore, the generated projection is displayed as a target indicator.

This provides the advantage that the generated projection provides visible information about a target positioning for the object. Thus, the user is provided with information about the relationship between the actual position of the object and a target position, or an index or set position. For example, in case the user is trying to move the object to a certain destination or desired position and rotation, by providing visual information about the actual position and the desired position, the user can derive spatial delta or difference from the displayed images such that the user can easily estimate necessary further movement steps in placing the object at the desired position.

It can be seen as the gist of the invention to determine the spatial positioning and rotation angle of an object and to provide this information in an intuitive way to the user such that the user is not distracted from other tasks, and thus to facilitate the user's understanding of the actual spatial situation with respect to the object of interest.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EXEMPLARY EMBODIMENTS

Figure 1:
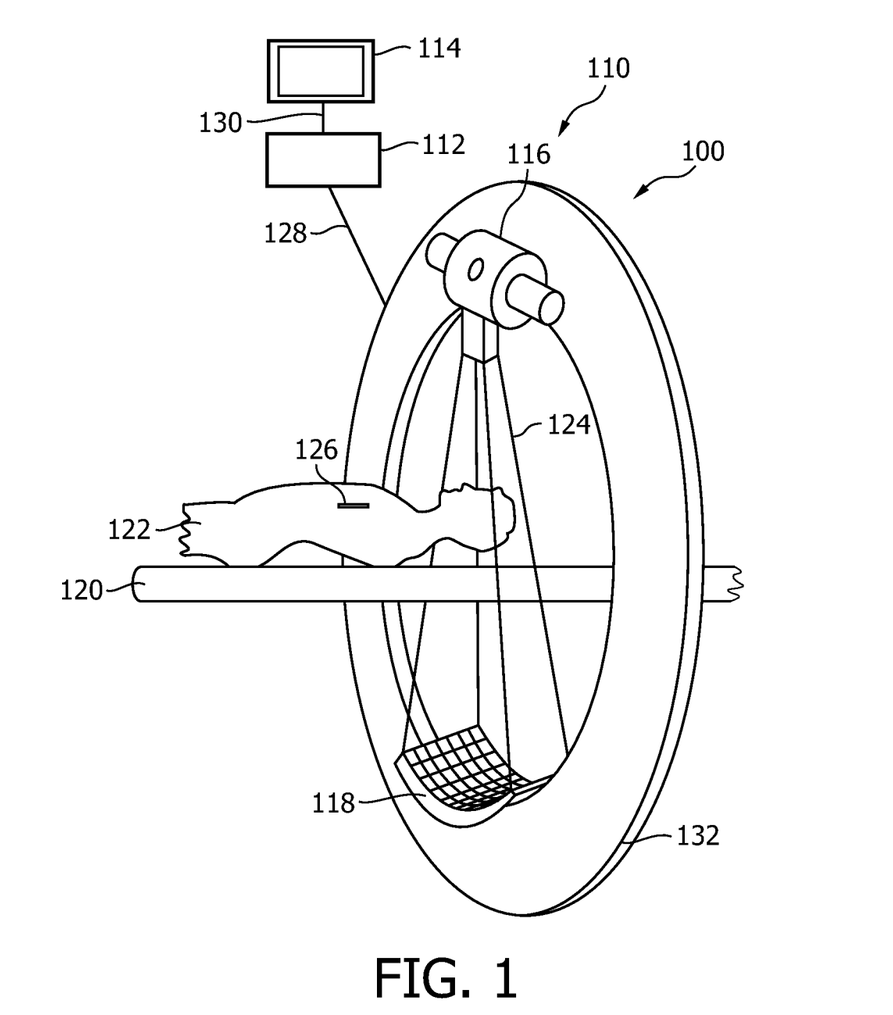
FIG. 1 illustrates a medical imaging system according to an exemplary embodiment of the invention.

In FIG. 1, a medical imaging system 100 is shown, the system comprising image acquisition means 110, a data processing unit 112, and a display 114. The acquisition means 110 comprise an X-ray source 116 and a detector arrangement 118. Further, a table 120 is provided on which an object of interest, for example a patient 122, can be arranged. For the acquisition by the acquisition means 110, the patient 122 on the table 120 can be arranged between the X-ray source 116 and the detector arrangement 118 such that X-rays 124 radiating from the X-ray source towards the detector arrangement 118 pass a region of interest of the patient 122.

Further, an object 126 is shown provided with at least three markers visible in a 2D image acquired by the acquisition means 110. It must be noted that the markers are not shown in FIG. 1. The acquisition means 110 are adapted to acquire 2D image data of an object, for example the object 126 with three markers. In the exemplary embodiment shown, the markers are radiopaque and thus visible in the X-ray image.

The acquisition means 110 are connected to the data processing unit, for example by a data connection 128. Thus, image data provided by the detector arrangement 118 is provided to the processing unit 112.

The data processing unit 112 is adapted to detect the markers in the 2D image and to identify the spatial positioning and rotation angle of the object, for example the object 126 with the markers, in relation to the system geometry on behalf of the markers.

In other words, the 2D image data is analyzed in the processing unit 112 and the markers visible in the 2D image are detected and used for further computing the spatial positioning and rotation angle of the object.

The data processing unit 112 is connected to the display 114 by a data connection 113.

Of course, the data connections 128 and 130 shown as a wire connection can also be provided as a wireless connection.

The display 114 is adapted to display an object indicator indicating the spatial positioning and rotation angle of the object. The object indicator is computed on behalf of the identified spatial positioning and rotation angle.

As can be seen from FIG. 1, the medical imaging system 100 is shown as a CT system with a gantry 132 on which the X-ray source 116 and the detector arrangement 118 can be rotated around the patient 122, thus generating also 3D image data.

It must be noted, that the medical imaging system could also be provided in another form, for example as a so-called C-arm system, on which the detector arrangement 118 and the X-ray source 116 are arranged on opposing ends of the C-arm, which C-arm can be moved, for example rotated, around the patient 122.

However, it is of course also possible to provide the medical imaging system with statically fixed image acquisition means, i.e. image acquisition means where the detector arrangement 118 and the X-ray source 116 are not movably mounted.

According to a further exemplary embodiment, the data processing unit 112 is also adapted to register a 3D image, for example acquired by the image acquisition means 110, with the 2D image data. Further, the display 114 is adapted to display the object indicator together with the image data of the registered 2D and 3D images.

According to a further exemplary embodiment of the invention, although not shown, the image acquisition means acquire 2D image data by the means of ultrasound. In such case, the object is provided with at least three markers visible in ultrasound image data, i.e. the markers are arranged such that ultrasound is reflected in a predetermined manner.

According to a further exemplary embodiment, also not shown, the above described image acquisition principles, i.e. X-ray, ultrasound or MR, can be combined, for example in an X-ray imaging system, where 2D image data is acquired by X-ray, and the markers are also visible in ultrasound or MR. Of course, any other combination is also possible.

Figure 2:
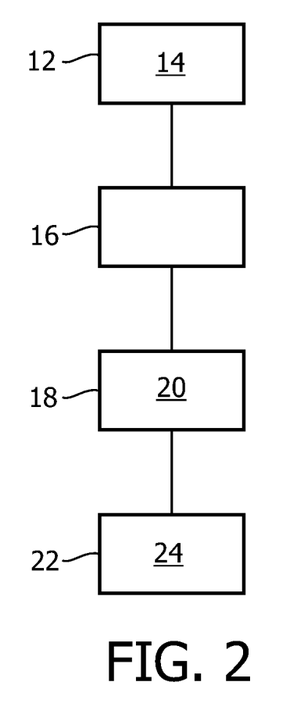
FIG. 2 schematically illustrates the basic steps of a method for operating a medical imaging system according to an exemplary embodiment of the invention.

In the following, the basic steps for a method for operating a medical imaging system, for example the medical imaging system 100 according to FIG. 1, are described with reference to FIG. 2.

In an acquisition step 12, 2D image data of an object is acquired with an imaging system. The object is provided with at least three markers visible in the 2D image (image data reference number 14). Further, in a detection step 16, the markers are detected in the 2D image. Then, in an identification step 18, the spatial positioning and rotation angle 20 of the object is identified in relation to the system geometry on behalf of the markers.

Following, in a display step 22, an object indicator 24 is displayed indicating the spatial positioning and rotation angle of the object, wherein the object indicator 24 is computed on behalf of the identified spatial positioning and rotation angle 20.

According to a further exemplary embodiment, although not shown, the object indicator 24 is a symbol indicating a central axis of extension of the model. Additionally, outer end points and/or the contour of the object can be shown.

According to another exemplary embodiment, the object indicator is a visualization of a model of the object. For example, the object indicator can also be a wireframe model of the object.

In case a medical imaging system 100 according to FIG. 1 is used, the 2D image data is acquired by X-rays, and the markers are radiopaque.

According to a further exemplary embodiment of the method, the 2D image data is acquired by ultrasound or MR, and the markers are visible in ultrasound image data or MR image data, and the object indicator is displayed in addition to an X-ray image, for example.

Figure 3:
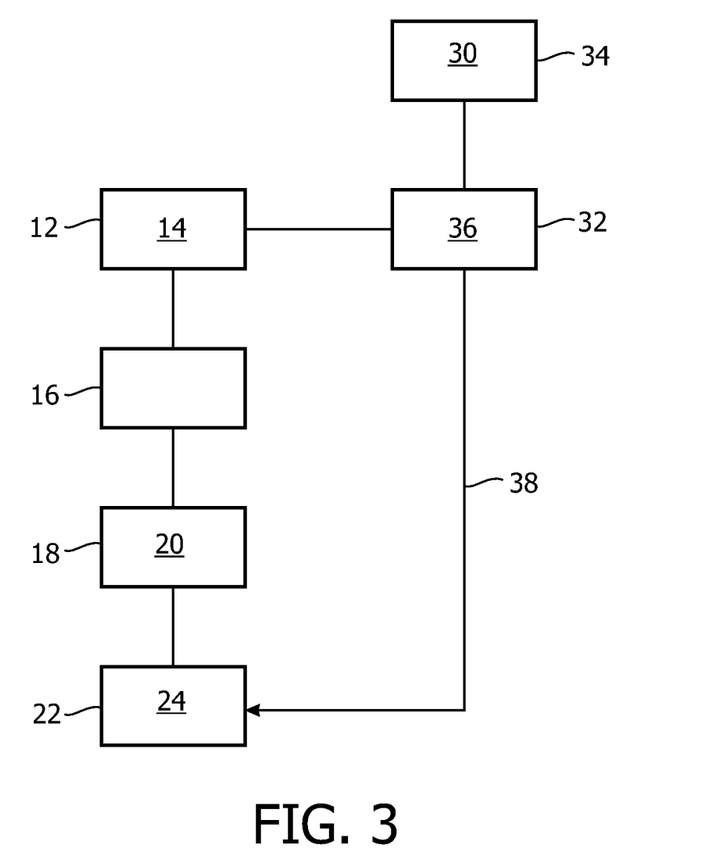
FIG. 3 describes steps of a method according to another exemplary embodiment of the invention.

According to an exemplary embodiment shown in FIG. 3, a 3D image is registered with the 2D image data 14 in a registration step 32. The 3D image, or image data 30, can, for example, be acquired before the acquisition step 12 in form of a pre-acquisition step 34.

According to another exemplary embodiment, the 3D image 30 is provided, for example, by a data bank stored in a memory.

As can be seen in FIG. 3, the object indicator 24 is displayed together with the image data of the registered 3D and 2D images 36 provided in the registration step 32, which displaying together is indicated by an arrow 38 entering the box of the display step 22.

According to a further exemplary embodiment, the 3D data 30 is an anatomical model extracted from acquired 3D image data, but which is not further shown in FIG. 3.

As already mentioned above, the object indicator 24 can comprise an indication of the object's contour.

According to a further exemplary embodiment, the object is an expandable object, and the object indicator comprises an indication of the object's contour in a final expanded state in addition to the object positioning and rotation angle.

For example, in case the object is a stent, the user is thus provided with the information where the stent and in which state the stent would be arranged, once the stent is opened. This can be useful for stent placing procedures, since the step of opening or expanding a stent cannot be reversed.

For example, the stent is applied via a catheter and that it only has two degrees of freedom, rotation and translation along the axis of the catheter. According to a further exemplary embodiment, the object is an elongated object, and the torsion of the object is detected on behalf of respective number of markers, and the torsion indicator is displayed, for example in combination with the object indicator (not further shown).

Figure 4:
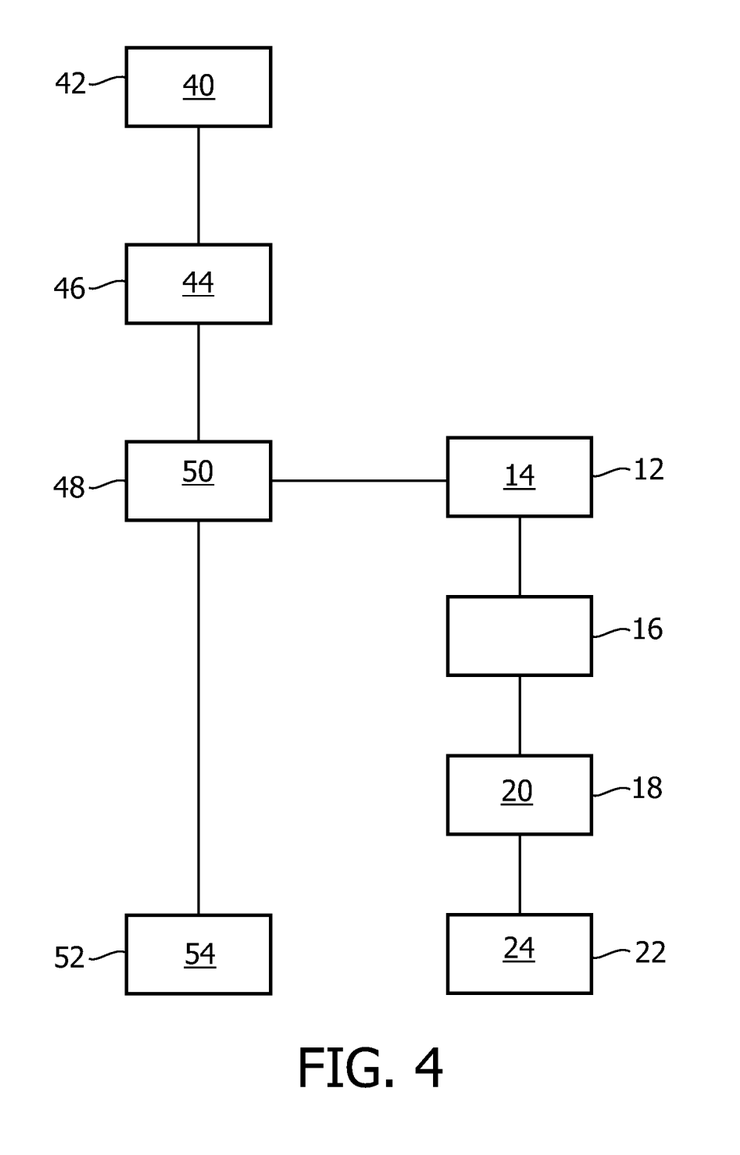
FIG. 4 describes method steps according to another exemplary embodiment of the invention.

According to a further exemplary embodiment, shown in FIG. 4, before the acquisition step 12, a desired spatial positioning and rotation angle 40 of the object are predetermined in a predetermination step 42. A configuration 44 of the markers is defined, respectively computed, from the position and rotation information of the object in a computing step 46 for the desired position 40.

Further, in a generating step 48, a projection 50 of the computed marker configuration 44 is generated according to the system geometry during the acquisition step 12 of the 2D image. The generated projection 50 is then displayed in a display step 52 as a target indicator 54.

As an example, the projection 50 can be a 2D projection.

Figure 5:
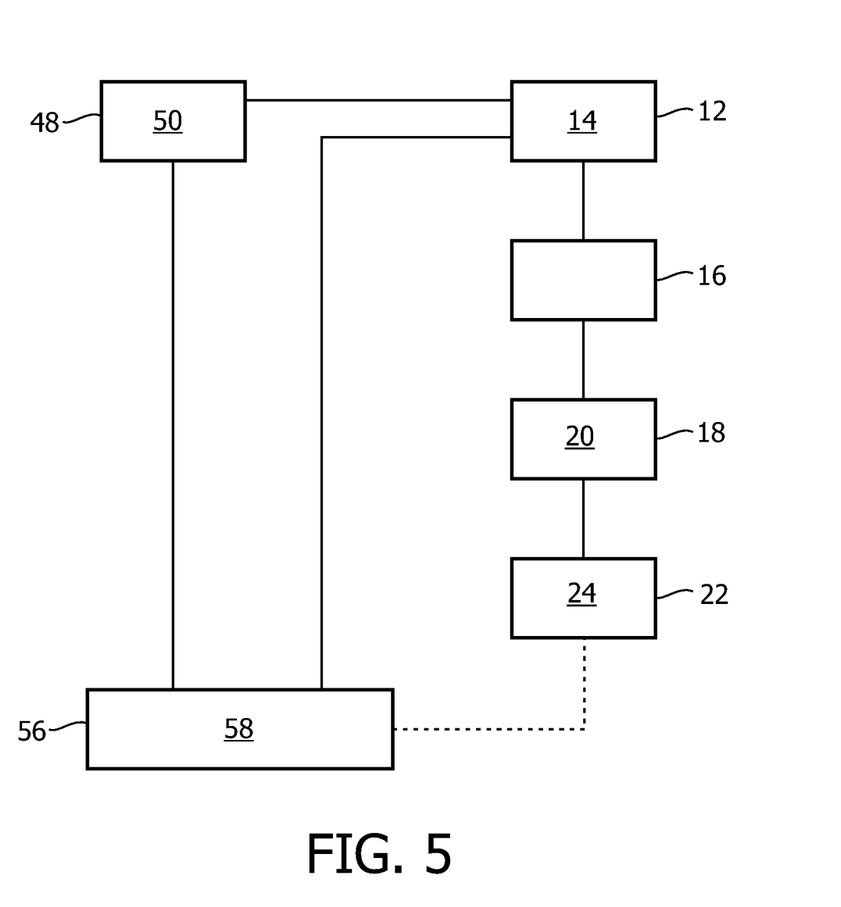
FIG. 5 describes a further exemplary embodiment of a method according to the invention.

According to a further exemplary embodiment, schematically described in FIG. 5, the generated projection 50 is overlaid with the 2D image in a combination step 56, thus providing an enhanced 2D image 58.

Figure 6:
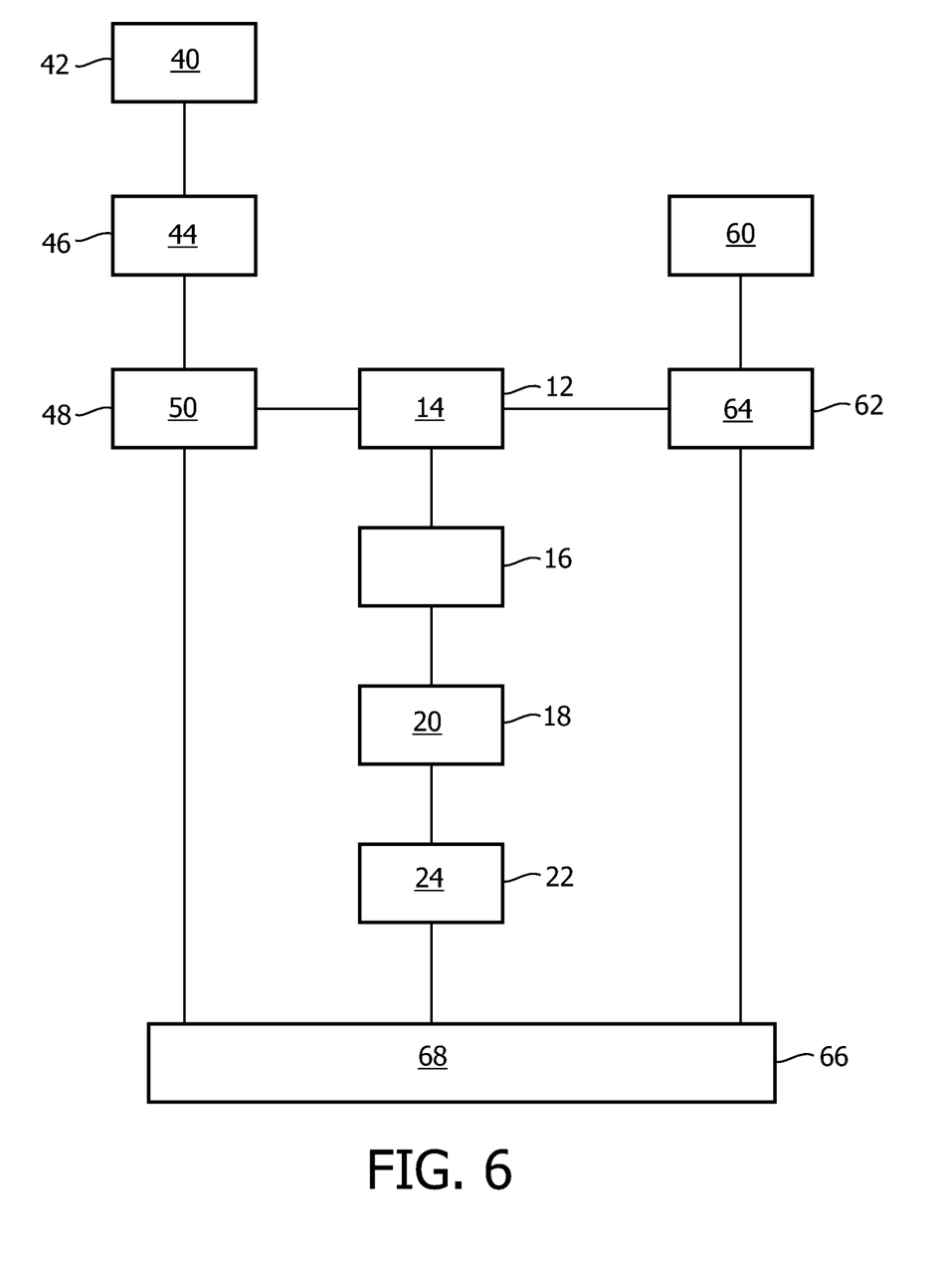
FIG. 6 describes a further exemplary embodiment of a method according to the invention.

According to a further exemplary embodiment, a 3D image 60 is registered with a 2D image data 14 in a registration step 62 and the generated projection 50 relating to the desired position is displayed together with the image data of the registered 3D and 2D images 64 in a combining display step 66, thus providing a further enhanced information image 68.

Figure 7:
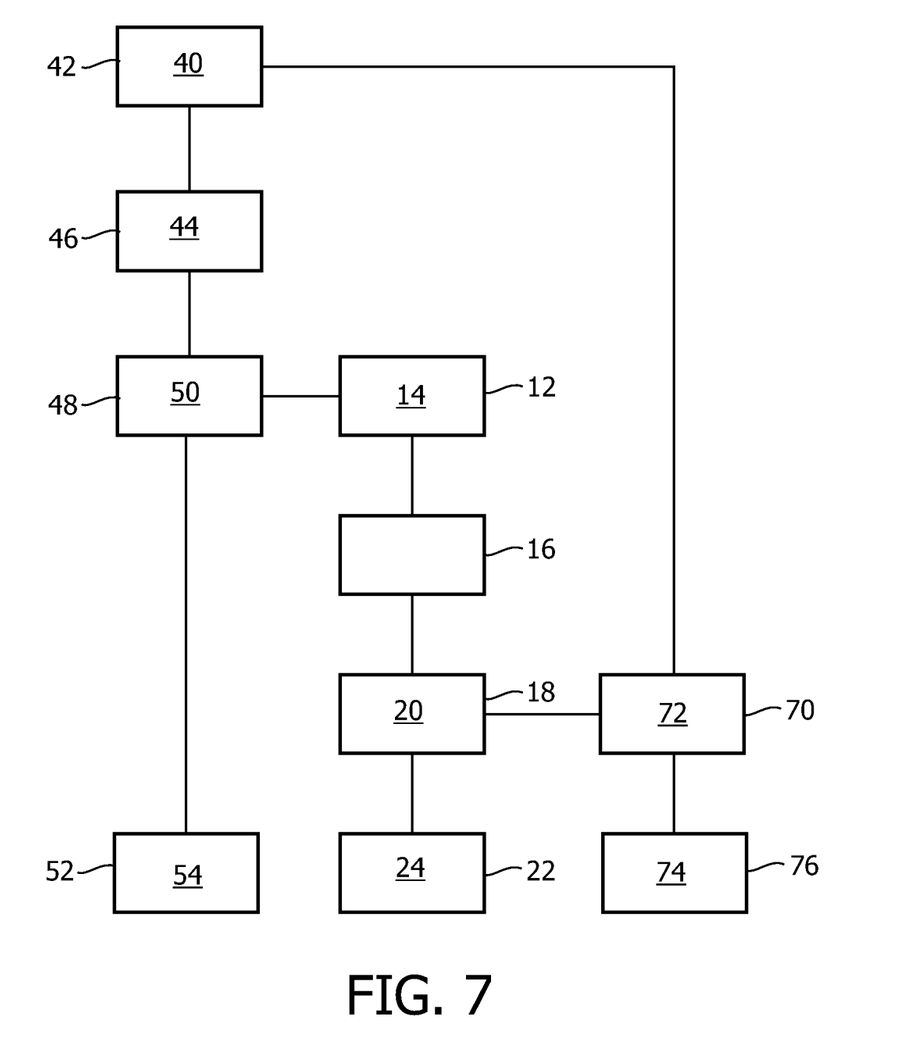
FIG. 7 describes a further exemplary embodiment of a method according to the invention.

According to a further exemplary embodiment shown in FIG. 7, the identified actual spatial positioning and rotation angle 20 of the object is compared with the predetermined spatial positioning and rotation angle 40 of the object in a comparison step 70, providing vector registration information 72. Further, on behalf of the vector registration information 72, a moving direction indicator 74 is provided in a generation step 76, and displayed such that maneuvering of the object is facilitated to the user.

For example, for maneuvering or moving the object to the desired or target position, the actual position and rotation angle is aligned with the predetermined position and rotation angle.

According to a further exemplary embodiment (not shown), the moving direction indicator 74 comprises a direction signal wherein the spatial orientation of the user is considered such that the direction signal indicates the actual direction of the movement by the user necessary to move the object towards the target position and orientation.

In other words, the user is provided with information in which direction he has to make a movement, for example of a manipulator, to achieve the correct positioning of the object.

For example, the object can be located inside a complexly structured volume and the manipulator can contact the object only from a certain destination or direction, the movement necessary by the user may be mirrored or opposite to the information shown on the display. In such a case, the direction signal provided to the user would give him or her direct instructions how to move without having to analyze the correct spatial relations of the present situation.

According to a further exemplary embodiment of the invention, an automatically positioning of the object is provided. Therefore, positioning data is provided such that a manipulating device can move the object to the desired or target position with the desired or target rotation.

Figure 8:
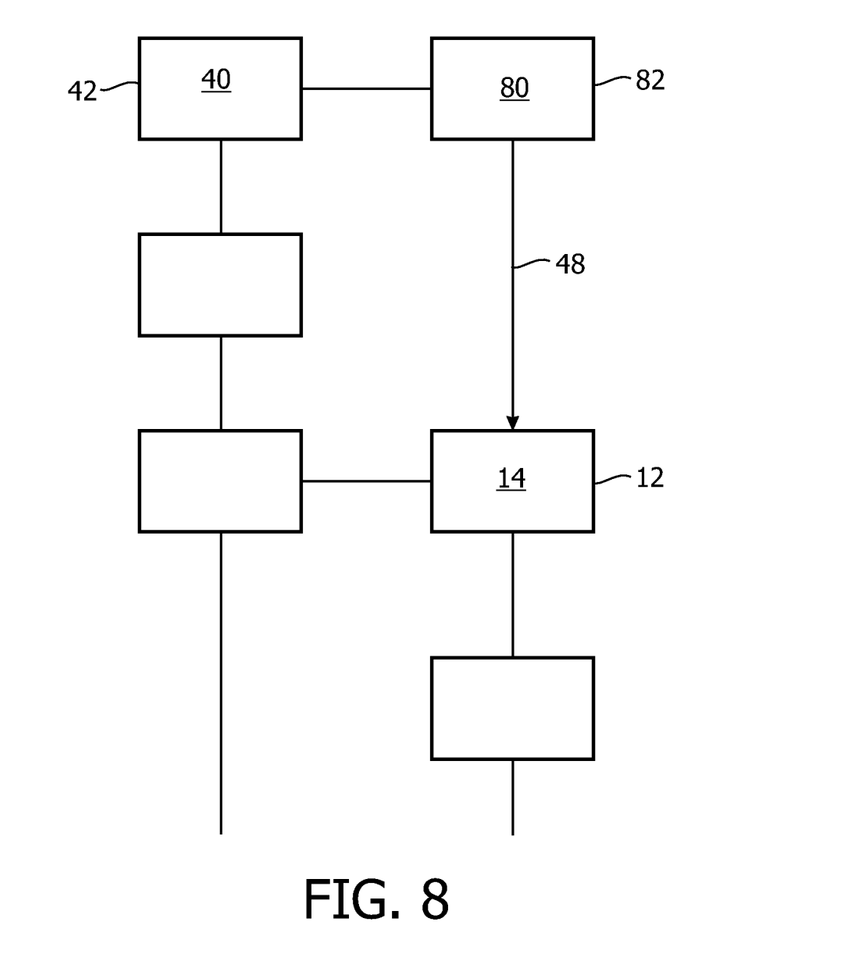
FIG. 8 describes a further exemplary embodiment of a method according to the invention.

According to a further exemplary embodiment, shown in FIG. 8, during the predetermination step 42, where the desired spatial positioning and rotation angle 40 of the object is predetermined, an optimal projection direction 80 for an acquiring 2D image data is determined in a determination step 82 on behalf of the predetermined spatial positioning and rotation angle of the object. The optimal projection direction 80 is then applied during the 2D image acquisition step 12, indicated by an arrow 84 entering the respective box of the acquisition step 12.

Figure 9:
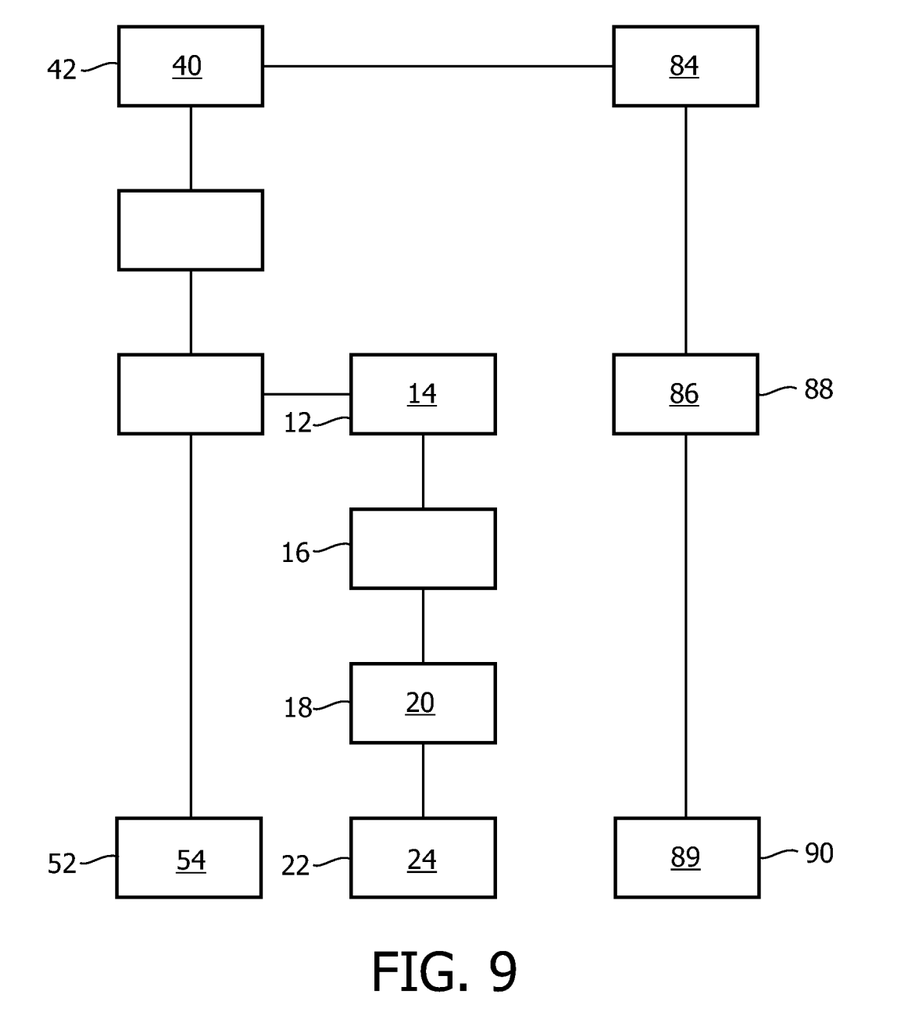
FIG. 9 describes a further exemplary embodiment of a method according to the invention.
Figure 10:
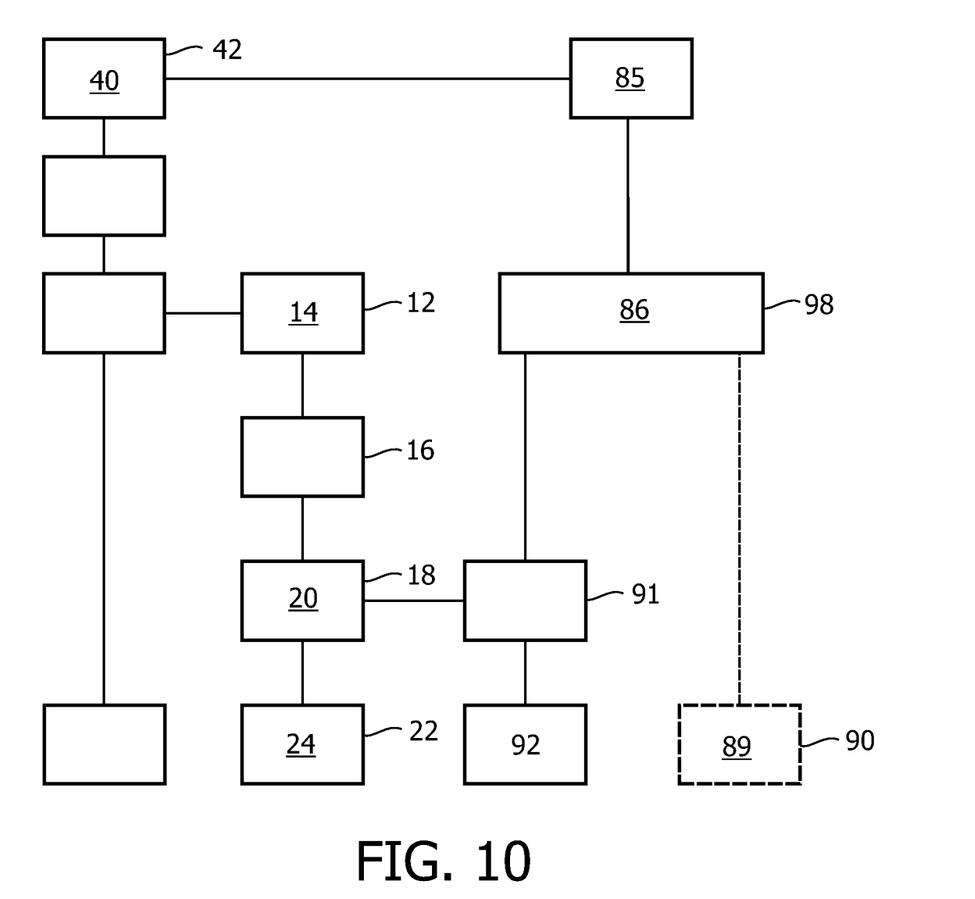
FIG. 10 describes a further exemplary embodiment of a method according to the invention.

According to a further exemplary embodiment, shown in FIG. 9, for at least one additional positioning and rotation angle 85, an additional configuration 86 is predetermined in a predetermination step 87. Further, the additional configuration 86 is displayed as additional information 89 in a display step 90.

For example, the additional configuration 86 relates to an unwanted orientation and position and the additional configuration 86 are displayed differently than the computed configuration in display step 52.

According to a further enhanced exemplary embodiment of the invention, the actual orientation and position, i.e. the spatial positioning and rotation angle 20, is compared with the additional configuration 86 in a comparison step 91 and a warning signal 92 is provided 93 in case of a predetermined degree of correlation.

As already indicated above, the object can, for example, be a stent which can be applied via a catheter. For example, the stent has only two degrees of freedom, rotation and translation along the axis of the catheter.

Figure 11:
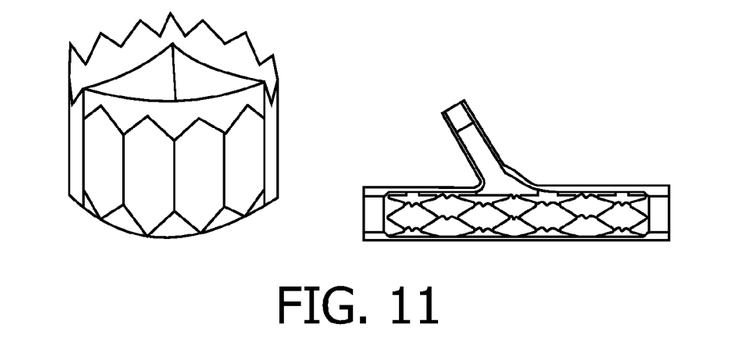
FIG. 11 shows exemplary embodiments of asymmetric objects.

Stents are getting more and more important; for example, nowadays, more and more vascular diseases can be treated minimally invasively under X-ray guidance. To achieve this, more and more complex stents have been developed for different applications: Stents with an artificial heart valve inside, stents with openings for side branches (fenestrated stents), branched stents for bifurcations, stents with a silk cover at the neck of an aneurism. An example for a coronary side branch stent is shown in FIG. 11.

In contrast to conventional stents, these stents are no longer actually symmetric and the stent has to be implanted in a certain rotation angle. However, due to the projective nature of imaging systems such as X-ray imaging systems, it is difficult to implant a stent in a predefined orientation.

Therefore, the above described exemplary embodiment assist in implanting a stent in a certain orientation.

The difficulty to determine the orientation of a stent from an X-ray is particularly the case if the stent has not yet been fully opened. For example, for the aortic valve stent, the valve leaflets are not visible in the X-ray image at all, and the stent itself is still actually symmetric. An example of the aortic valve stent is also shown in FIG. 11.

According to a further aspect of the invention, the above described method steps shall be explained in relation with an aortic valve stent as an example. However, embodiments for other applications would be similar.

Figure 12:
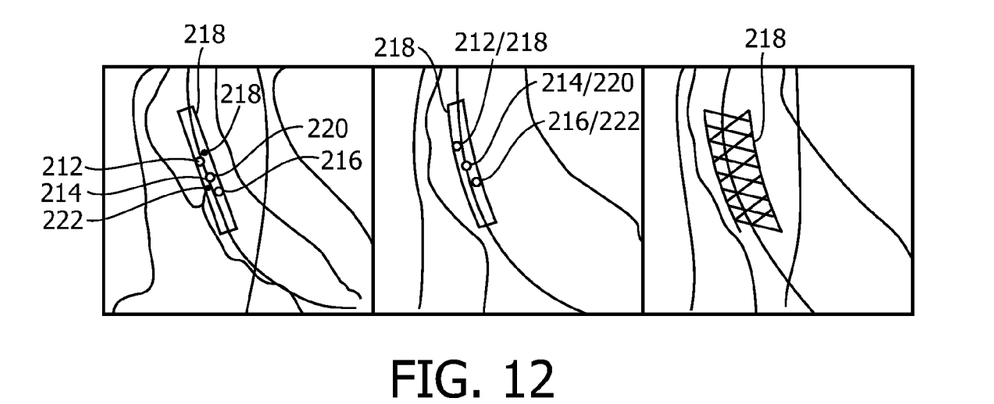
FIG. 12 shows 2D images according to an exemplary embodiment of the invention.

According to an embodiment shown in FIG. 12, in a planning step, the desired position and orientation of a stent has been determined. As an example, this can either be done manually or a 3D segmentation can be used to compute the optimal position and orientation of the stent automatically. From this, as mentioned above, the desired 3D position of the markers can be computed.

During the intervention, the information about the geometry of the X-ray system, the location of the patient and the desired location of the stent and its markers, is used to compute the target projection points. These are overlaid onto the X-ray image, shown in FIG. 12A, where the target projection points are indicated by small circles 212, 214, and 216. Thus, the user is provided with the target position of the markers. In FIG. 12, a stent 218 is shown with three visible markers indicated with reference numbers 220, 222, and 224. As can be seen from FIG. 12A, only one of the markers, namely marker 220 is aligned with one of the target projection points, namely circle 214. Thus, the user is provided with information about the relation between the actual position and the target position of the stent 218. Then, the user can move the stent according to the information retrieved from FIG. 12A. The result from the correct adjustment of the rotation angle is shown in FIG. 12B. It must be noted that the markers 220, 222, and 224 are aligned with the respective target positions 212, 214, and 216. Thus, the user is provided with the information that the stent 118 is now in the correct position as well as in the correct orientation, i.e. rotation angle, and as a next step, the user can open the stent, since it is in its final, i.e. desired, position. The result of an opened stent is shown in FIG. 12C.

According to the exemplary embodiments of the method described above, it is also possible to display the current orientation of an implant, for example a stent, in relation with a target orientation.

Figure 13:
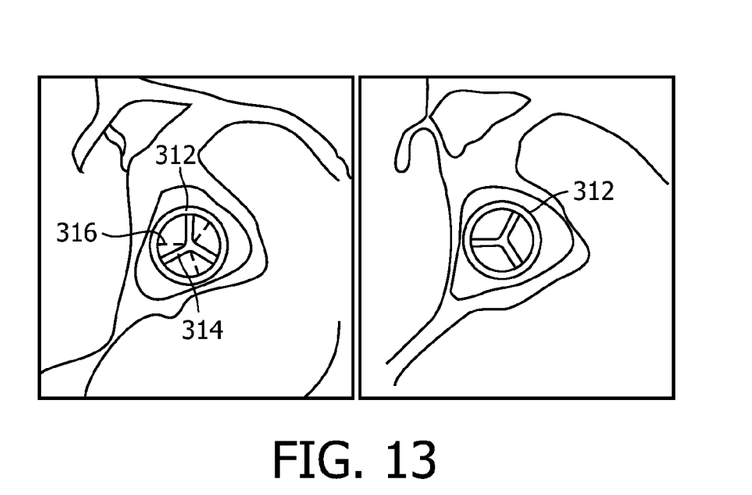
FIG. 13 shows 2D images according to another exemplary embodiment of the invention.

As can be seen in FIG. 13, a cross-sectional image of an aortic valve and bulbus is shown in combination with an inserted stent, indicated with a visualization of a model of the stent in an opened version which is shown as a circle 312 including three radial lines 314 symbolizing the heart valve arrangement.

During the intervention, the markers are tracked, as described above. Then, the geometric information of the X-ray system, the relative 3D position of the markers to each other, and the information about the projection points of the markers in the X-ray image is used to determine the 3D position of the markers.

From this, the current orientation of the stent can be reconstructed and the result can be displayed in a 3D image as exemplarily shown in FIG. 13. Besides the actual position of the stent 312, the user is provided with the information how the stent would be placed in the opened state by a model shown. For a correct rotation, a desired or target position is indicated with target indication symbol 316, for example dashed lines representing the heart valve structure. As can be seen from FIG. 13A, the actual position and the desired position are not aligned yet, whereas in FIG. 13B, after the adjustment of the rotation angle, the generated projection indicated by the target indicator 316 is overlaid by the model representing the stent in the final state 312. Hence, the user is provided with the information that the stent is now in the correct position and can thus be opened. Of course, for the correct positioning in the length direction, which is not visible in the cross section according to FIG. 13, the user can also be provided with the respective information, for example in a length cross section which is not further shown.

According to an exemplary embodiment of the invention, the markers should be positioned at different heights and different angles of the object. If they are placed at different heights, they cannot overlap in a view with no foreshortening of the object and it is easier to distinguish them. The placing at different angles provides the advantage that only two orientations can give a match of the markers in a 2D image. Uniqueness of the match can be achieved when it is known which marker is nearest or when, for example, a false marker is added or when the three markers can be distinguished from each other.

In another exemplary embodiment of the present invention, a computer program or a computer program element is provided that is characterized by being adapted to execute the method steps of the method according to one the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention, and a computer program that by means of an update turns an existing program into a program that uses the invention. Further on, the computer program element might be able to provide all necessary steps to fulfill the procedure of an exemplary embodiment of the method as described above. According to a further exemplary embodiment of the present invention, a computer readable medium, such as a CD Rom is presented wherein the computer readable medium has a computer program element stored on it which computer program element is described by the preceding section.

A computer program may be stored and/or distributed on a suitable medium, such as optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It must be noted that embodiments of the invention are described with reference to different subject-matters. In particular, some embodiments are described with reference to method type claims, whereas other embodiments are described with reference to the device type claims. However, a person skilled in the art will gather from the above and the following description that, unless otherwise notified, in addition to any combination of the features belonging to one type of subject-matter also any combination between features relating to different subject matters is considered to be disclosed with this application. However, all features can be combined providing synergetic effects that are more than the simple summation of the features.

In the claims, the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in claims should not be construed as limiting the scope.

The invention claimed is:

1. A medical imaging system comprising:
    image acquisition means;
    a marker-based object position and orientation determination module; and
    a display,
    wherein said acquisition means is configured to acquire a two-dimensional (2D) image of an object, wherein said object is provided with at least three markers visible in the 2D image;
    wherein said determination module is configured to detect said markers in said 2D image; to identify, on behalf of said markers, both a spatial positioning and rotation angle of said object in relation to geometry of said system; to compute a configuration of said markers for a targeted spatial positioning and rotation angle; to, during the acquisition of said 2D image, generate a projection of the computed configuration according to the system geometry; and to, via said display, display both an object-indicator indicating the identified spatial positioning and rotation angle of said object and, as a target indicator, the generated projection.

2. The system according to claim 1, wherein said 2D image is acquired by X-rays and wherein said markers are radiopaque.

3. The system according to claim 1, said determination module being further configured to register wherein a 3D image with said 2D image and to, via said display, display said object-indicator together with image data of the registered 3D and 2D images.

4. The system according to claim 3, wherein said 3D image comprises an anatomical model extracted from 3D image data acquired via said image acquisition means.

5. The system according to claim 1, a medical instrument comprising said object, wherein said object is an elongated object and wherein said determination module detects torsion of said object and displays, via said display, a torsion indicator.

6. The system according to claim 1, wherein said determination module is further configured to overlay said generated projection over said 2D image.

7. The system according to claim 1, wherein said determination module is further configured for:
    a) determining, on behalf of said targeted spatial positioning and rotation angle, an optimal projection direction for the acquiring; and
    b) applying said optimal projection direction during said acquisition.

8. The system according to claim 1, wherein said determination module is configured for determining, prior to said acquisition, an additional configuration for at least one additional positioning and rotation angle and for displaying the additional configuration.

9. The system of claim 8, wherein said determination module is further configured for comparing said additional configuration to said spatial positioning and rotation angle of said object.

10. The system of claim 9, wherein said comparing comprises correlating, said determination module being further configured for issuing a warning signal in case a correlation exceeds a predetermined level.

11. The system of claim 1, said determination module being further configured for the computing of said configuration prior to said acquisition.

12. The system of claim 11, said configuration comprising a 3D configuration.

13. The system of claim 12, said projection being a 2D projection.

14. The system of claim 1, said determination module being further configured for, via said display, providing a moving direction indicator such that interactive maneuvering of the object toward a targeted spatial positioning and rotation angle is facilitated.

15. The system of claim 14, said object comprising a physical object.

16. The system of claim 1, wherein said object is a physical object that is expandable into an expanded state, said object having a contour depicting said object in said state, the displayed object-indicator further indicating said contour.

17. A method for operation of a medical image system, comprising the following steps:
    a) acquiring 2D image data of an object with an imaging system; wherein the object is provided with at least three markers visible in the 2D image;
    b) detecting the markers in the 2D image;
    c) identifying the spatial positioning and rotation angle of the object in relation to the system geometry on behalf of the markers; and
    d) displaying an object-indicator indicating the spatial positioning and rotation angle of the object, wherein before step a), a desired spatial positioning and rotation angle of the object is predetermined and wherein a configuration of the markers for the desired position is computed; wherein a projection of the computed marker configuration is generated according to the system geometry during the acquisition of the 2D image in step a); and wherein the generated projection is displayed as a target indicator.

18. A medical imaging system comprising:
    image acquisition means;
    a marked-object position and orientation determination module; and
    a display,
    wherein said acquisition means is configured to acquire a two-dimensional (2D) image of an object, wherein said object is provided with at least three markers visible in the 2D image;
    wherein said determination module is configured to detect said markers in said 2D image; to identify, on behalf of said markers, spatial positioning and rotation angle of said object in relation to geometry of said system; to, via said display, display an object-indicator indicating the identified spatial positioning and rotation angle of said object; and to, via said display, provide, in addition to said object-indicator and an indicator of a targeted spatial positioning and rotation angle of said object, a moving direction indicator such that maneuvering of said object toward targeted spatial positioning and rotation angle is facilitated.

19. The system of claim 18, said object comprising a physical object.

20. The system of claim 18, said maneuvering being interactive, said providing of said moving direction indicator being iterative.

21. The system of claim 18, said moving direction indicator comprising a direction signal, said determination module forming said signal based on a spatial orientation of a user of said system such that said maneuvering is facilitated by an actual direction of movement by the user for said maneuvering.

22. A non-statutory computer readable medium embodying a computer program for a medical system, said program having instructions executable by a processor for performing a plurality of acts, among said plurality there being the acts of:
   a) acquiring a 2D image of an object with an imaging system; wherein the object is provided with at least three markers visible in the 2D image;
   b) detecting the markers in the 2D image;
   c) identifying the spatial positioning and rotation angle of the object in relation to the system geometry on behalf of the markers; and
   d) displaying an object-indicator indicating the spatial positioning and rotation angle of the object, wherein before act a), a desired spatial positioning and rotation angle of the object is predetermined and wherein a configuration of the markers for the desired position is computed; wherein a projection of the computed marker configuration is generated according to the system geometry during the acquisition of the 2D image in act a); and wherein the generated projection is displayed as a target indicator.

23. The computer readable medium of claim 22, among said plurality there being the further act of displaying a moving direction indicator such that interactive maneuvering of the object toward a targeted spatial positioning and rotation angle is facilitated.

* * * * *